United States Patent
Rubinsky

Patent Number: 6,032,675
Date of Patent: Mar. 7, 2000

[54] FREEZING METHOD FOR CONTROLLED REMOVAL OF FATTY TISSUE BY LIPOSUCTION

[76] Inventor: Boris Rubinsky, 1619 Sonoma Ave., Albany, Calif. 94707

[21] Appl. No.: 09/042,835

[22] Filed: Mar. 17, 1998

Related U.S. Application Data

[60] Provisional application No. 60/040,859, Mar. 17, 1997.

[51] Int. Cl.[7] ................................................. A61B 17/32
[52] U.S. Cl. ............................... 128/898; 606/20; 604/35
[58] Field of Search ................... 128/898; 606/20–26; 604/35, 28

[56] References Cited

U.S. PATENT DOCUMENTS

| 3,827,436 | 8/1974 | Stumpf et al. |
| 5,433,717 | 7/1995 | Rubinsky et al. ................... 606/20 |
| 5,472,416 | 12/1995 | Blugerman et al. ................. 604/28 |
| 5,603,221 | 2/1997 | Maytal . |
| 5,651,773 | 7/1997 | Perry et al. ........................ 604/174 |
| 5,746,736 | 5/1998 | Tankovich ............................ 606/9 |
| 5,817,050 | 10/1998 | Klein ................................... 604/35 |
| 5,833,685 | 11/1998 | Tortal et al. ........................ 606/23 |

FOREIGN PATENT DOCUMENTS

WO 97/05828   2/1997   WIPO .

*Primary Examiner*—Michael Peffley
*Attorney, Agent, or Firm*—Testa, Hurwitz & Thibeault, LLP

[57] ABSTRACT

A method for removing fatty tissue in a body combines cryosurgery and liposuction. Cryosurgery first destroys fatty tissue to be removed by controllably freezing the tissue, and facilitates removal of the fatty tissue. Liposuction subsequently removes the destroyed fatty tissue by aspiration.

18 Claims, 2 Drawing Sheets

FREEZING METHOD FOR CONTROLLED REMOVAL OF FATTY TISSUE BY LIPOSUCTION

RELATED APPLICATIONS

This application claims priority to provisional application U.S. Ser. No. 60/040,859 filed on Mar. 17, 1997.

FIELD OF THE INVENTION

The invention relates to liposuction and, more specifically, relates to an apparatus and method for destroying and removing fatty tissue in a body.

BACKGROUND OF THE INVENTION

The skin insulates and protects the entire body from mechanical, chemical and thermal damage. Beneath the dermis is the subcutaneous tissue which contains many fat cells. The subcutaneous tissue serves as a "shock absorber" and insulates the deeper tissues from extreme temperature changes. The subcutaneous tissue is also responsible for the outer appearance of the body surface. Another major function of the fat cells is to accumulate fat, as a means for storing food. However, for cosmetic or aesthetic reasons, it may be desirable to reduce the volume of fatty tissue in the body. Exercise and diet can sometimes reduce accumulation of fat in the fat cells, but they cannot reduce the number of fat cells or their distribution. The number of fat cells in the subcutaneous tissue is relatively constant. Furthermore, fat accumulation persists despite diet or exercise for many people.

Liposuction is a surgical procedure that permanently removes localized deposits of fat cells, thereby producing a desirable shape of the body or the face through sculpturing. In a typical liposuction, a catheter connected to a high vacuum device is introduced into the fatty tissue through an incision in the skin, and the fat is removed by aspiration. This procedure requires general anesthesia, involves significant blood loss, and has relatively high morbidity and mortality. This problem has been resolved to some extent with the more recent tumescent liposuction. In tumescent liposuction, large volumes of dilute lidocaine and epinephrine are infiltrated into the subcutaneous fatty tissue before the suction stage. Lidocaine and epinephrine are delivered through a canulated hollow tube inserted through a small skin incision into the fatty tissue between the skin and the muscle. Lidocaine is a local anesthetic, and epinephrine causes lipolysis and vasoconstriction. Lipolysis is destruction of fatty structures. Following the infiltration of the mixture of lidocaine and epinephrine, a catheter connected to a high vacuum device is introduced to the fatty tissue and moved rapidly through the tissue to break up the fat cells that are aspirated through the catheter. This procedure has significantly less morbidity and has no reported mortality.

During the aspiration part of the liposuction procedure, the surgeon tries to remove the fatty tissue in such a way that a desired sculpted tissue structure is achieved. During this step, it is important not only to remove the fat from the various areas to obtain the desired shape, but also to create a final tissue appearance of the skin that is regular and smooth. Creating a smooth final tissue appearance, however, is not an easy task. The sculpting of the tissue and the final aesthetic appearance of the body are strongly dependent on the technical skill of the surgeon.

Cryosurgery is a procedure for destroying tissue. In cryosurgery, undesirable tissues are frozen and destroyed. The technique is minimally invasive, usually requiring an insertion of only one or more thin, cylindrical, cryosurgical probes into the undesirable tissue. The probes are cooled internally with a cryogen and are insulated except at the tip. The uninsulated tip is inserted in a tumor or other undesirable tissue, and the tissue is frozen from the probe surface outward. When the desired amount of tissue has been frozen, cryogen is prevented from flowing to the probe, and the tissue is allowed to thaw. After cryosurgery, the frozen tissue is left in situ to be reabsorbed by the immune system over time. Since freezing originates from small uninsulated tip of a probe, the procedure can be confined to a region of the diseased tissue, thereby sparing surrounding healthy tissue. The freezing process can be precise and controlled, as the freezing interface is sharp and propagates slowly (in the order of mm/min). A small probe having a diameter of around 3 mm can produce a 3.5 cm ice ball, and therefore treat a relatively large tissue region. When the shape of the pathological tissue is large and complex, several probes can be used simultaneously to generate a frozen region of a desired shape. For example, prostate and liver cryosurgery is currently performed with five 3 mm diameter probes. Multiple sites can be treated separately or together. Because the only physical invasion of the tissue is the insertion of the cryoprobes, cryosurgery does not create a lot of complications and patient morbidity is low. Cryosurgery can produce excellent medical results with less distress and disfiguration at a lower cost. In addition, cryosurgery is not dose limited, therefore retreatment is possible.

Until recently, a major impediment to the extensive use of cryosurgery on internal tissues has been the inability to observe the frozen region deep inside the body, which could cause complications of over or under freezing. Breakthroughs in non-invasive imaging technology, however, have made possible major advances in cryosurgery in general and prostate and liver cryosurgery in particular. Intraoperative ultrasound can image the progress of freezing during cryosurgery by virtue of the fact that the interface between frozen tissue and non-frozen tissue is associated with a change in acoustic impedance that reflects ultrasound waves. Cryosurgery is now almost universally carried out under ultrasound guidance. Another recent improvement in imaging technology for use with cryosurgery is magnetic resonance imaging (MRI). This technique, which images the process of freezing in three dimensions, can monitor the freezing interface with a resolution of 200 gm, and can control its shape through MRI feedback. Additional methods of imaging are being continuously developed. One such method under development is the use of light to image freezing. Cryosurgery can be performed with greater accuracy and control with the assistance of the imaging techniques. Therefore, cryosurgery is gaining acceptance as a first-line therapy for prostate, liver and other cancer therapy.

Mazur's two factor theory explains destruction of tissue by freezing. Much of the research on the effects of freezing on biological materials has focused on the use of freezing for preservation of cells (such as red blood cells, embryos, sperm). This work has shown that an important thermal variable is the cooling rate (change in temperature per unit time) during freezing. The correlation between cell survival and cooling rate is an "inverse U" shape. Cell survival is greatest for the cooling rate at the peak of the inverse "U", and destruction increases above or below this optimal cooling rate for survival. However, different types of cells have different optimal cooling rates for survival. This difference is associated with the structure and mass transfer properties of the cell membrane and the size of the cells. These general findings are incorporated in Mazur's "two factor" theory, which explains how cooling rates relate to cellular damage.

Mazur proposed that since the probability for an ice crystal to form at any temperature is a function of volume during freezing of cells in a cellular suspension, ice will form first in the much larger extracellular space, before each individual cell freezes. Since ice does not incorporate solutes, the ice that forms in the extracellular space will reject the solutes into the remaining unfrozen solution. The concentration of solutes in the extracellular solution will consequently increase. The small volume of intracellular solution results in a correspondingly low probability for ice nucleation to occur inside the cell. Therefore, with sufficiently low cooling rates, the intracellular solution can remain supercooled and unfrozen, when the extracellular solution begins to freeze and exclude solutes. Under these circumstances, the unfrozen cells will be surrounded by a hypertonic solution. To equilibrate the difference in chemical potential between the intracellular and the extracellular solution, water will pass through the cell membrane, which is permeable to water but impermeable to ions and other organic solutes. Therefore, as the temperature of the solution is lowered and additional ice forms in the extracellular solution, water will leave the cell to equilibrate the intracellular and the extracellular concentration, and the cell will dehydrate and shrink. The intracellular solution will remain unfrozen and become hypertonic, causing chemical damage involving denaturation of intracellular proteins. Since chemical damage is a function of time and temperature, the damage will increase with lower cooling rates. Because water transport is a rate dependent process, faster freezing with higher cooling rates decreases the amount of time a cell is exposed to the chemically damaging conditions and increases survival. This explains the increase in cell viability with an increase in cooling rate toward an optimum. However, increasing the cooling rate also results in a more rapid decrease in temperature. The unfrozen water in cells will therefore experience a greater thermodynamic supercooling. The supercooled intracellular solution is thermodynamically unstable, and after reaching a certain value it will nucleate and freeze. It is thought that the intracellular ice formation damages cells. The probability for intracellular ice formation increases with increasing cooling rate, and consequently the survival of frozen cells decreases with increasing cooling rate.

These two modes of damage, chemical at low cooling rates and intracellular ice formation at high cooling rates, form the basis of the "two factor" theory of cellular damage proposed by Mazur. Survival of cells is optimal during freezing with thermal conditions in which these two conflicting modes of damage are minimized.

An object of this invention is to develop a method, and the related apparatus to further reduce the morbidity associated with liposuction and to facilitate greater control over the appearance of the body surface after liposuction. The invention combines cryosurgery with liposuction.

SUMMARY OF THE INVENTION

In one aspect, the invention features a novel method for removing fatty tissue in a body. According to the method, fatty tissue is first destroyed and subsequently removed from the body. In one embodiment, fatty tissue is first destroyed using cryosurgery, and the destroyed fatty tissue is subsequently removed using a conventional liposuction procedure. Destruction of the fatty tissue prior to liposuction facilitates the removal step. In another embodiment, fatty tissue is destroyed using cryosurgery, and the destroyed tissue is left in the body for the body's natural immune system to remove.

In one embodiment, a cryosurgical probe is inserted in the fatty tissue, and the probe is internally cooled with a cryogen. The cryosurgical probe freezes the fatty tissue at a rate which propagates the freezing interface in the order of approximately several millimeters per minute. In another embodiment, the freezing process is monitored to control the extent of freezing. Monitoring may be performed using palpation, image monitoring or temperature monitoring.

In still another embodiment, heat is applied to a skin area surrounding the fatty tissue during the freezing process in order to prevent the skin area from freezing. Heat may be applied to the skin area by placing a warm pad perfused with warm fluid on surfaces of monitoring probes, and placing the monitoring probes on the body prior to inserting the cryosurgical probe into the fatty tissue. In still another embodiment, a tumescent fluid is introduced in the fatty tissue prior to freezing the fatty tissue. The tumescent fluid functions as an anesthetic and also assists in destroying the fatty tissue. An example of a tumescent fluid is combination of lidocaine and epinephrine.

In another aspect, the invention features an apparatus for removing a fatty tissue inside a body. The apparatus includes a first probe for freezing and destroying the fatty tissue and a second probe for removing the destroyed fatty tissue. In one embodiment, the first probe comprises a cryosurgical probe internally cooled with a cryogen, and the second probe comprise a conventional liposuction probe. The cryosurgical probe may be a thin cylindrical probe insertable in a tissue and connected to a source of cryogen. The liposuction probe may be an aspiration needle connected to a source of vacuum. In another embodiment, the first probe and the second probe are assembled into a single unit. The second probe, for example, comprises an outer sleeve surrounding an inner probe. The inner probe is the first probe.

In still another embodiment, the apparatus includes a third probe for inserting a tumescent fluid into the fatty tissue. In still another embodiment, the apparatus includes monitoring probes in communication with a monitor for monitoring the freezing process.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which.

DETAILED DESCRIPTION

Figure 1:
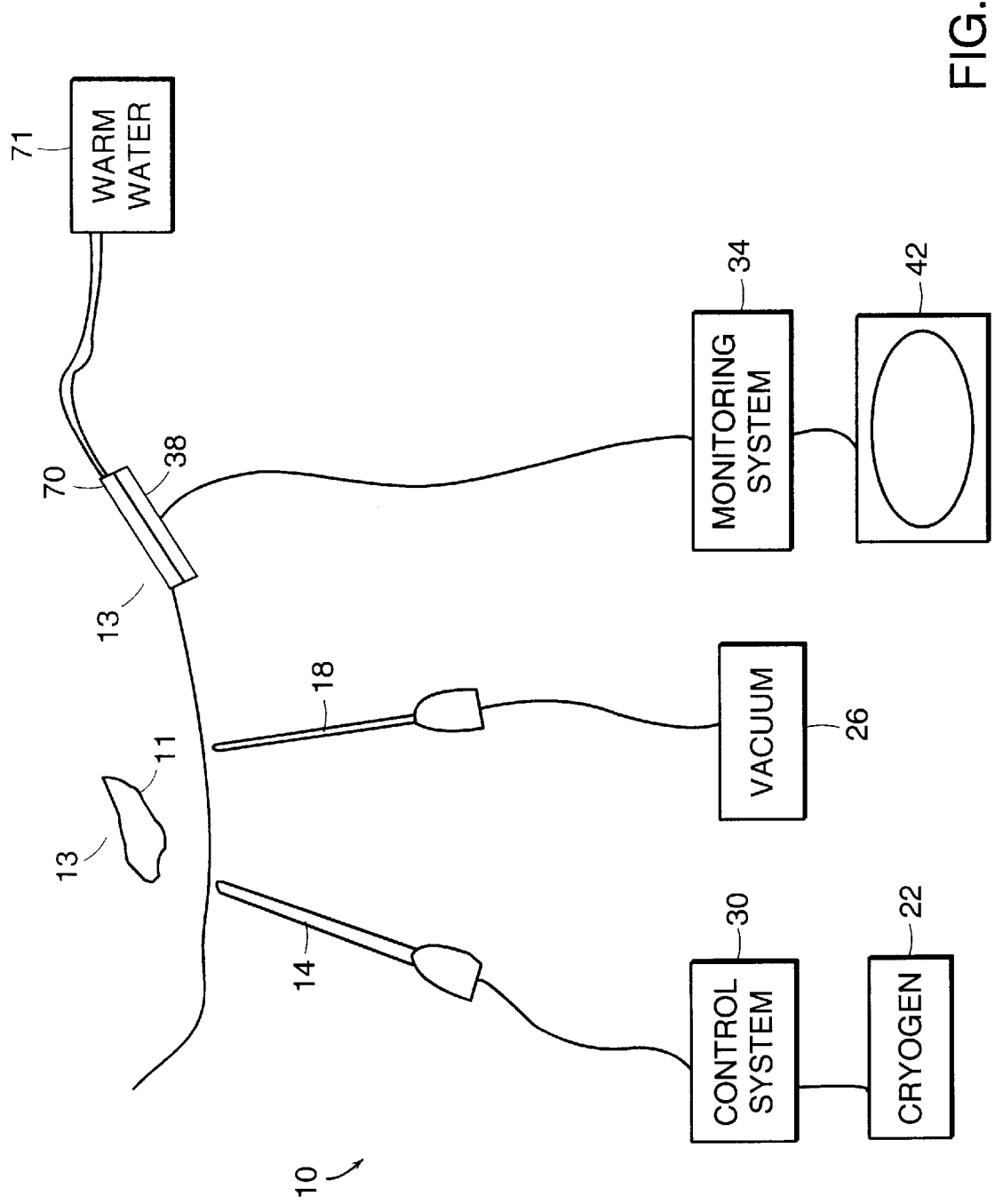
FIG. 1 shows one embodiment of a cryoliposuction apparatus of the present invention.

Referring to FIG. 1, a cryoliposuction apparatus 10 includes a first probe 14 for freezing and destroying fatty tissue, and a second probe 18 for removing the destroyed fatty tissue. In one embodiment, the first probe 14 is a cryosurgical probe which is internally cooled with a cryogen. The cryosurgical probe 14 may be in communication with an external source of cryogen 22. Alternatively, the cryosurgical probe 14 may include the cryogen inside the probe 14. In one embodiment, the first probe 14 is shaped to facilitate the destruction of fatty tissue, without contacting surrounding tissue or skin. The first probe 14, for example, comprises a thin cylindrical probe insertable in tissue. The thin cylindrical probe 14, may have a diameter of approximately several millimeters. The cryosurgical probe 14 and the cryogen 22 may be in communication with a controller 30 to control the amount of cryogen delivered to the probe 14. According to the invention, the cryosurgical probe 14 may be any conventional cryosurgical probe known in the art capable of cooling tissue upon contact.

In one embodiment, the second probe 18 comprises a conventional liposuction probe. A conventional liposuction probe 18 includes an aspiration needle in communication with an external source of vacuum 26 such as a vacuum pump.

The cryoliposuction apparatus 10 may further include a monitoring system 34. The monitoring system 34 includes one or more monitoring probes 38 in communication with a monitor 42. The monitoring probes 38 contact the body during the cryoliposuction process and monitors the freezing process. In one embodiment, the monitoring probes 38 are ultrasound surface probes, and the monitor 42 is an ultrasound imaging machine. Ultrasound imaging technique is well known to those skilled in the art. Other imaging techniques such as light imaging, MRI, ultrasound, and thermocouples, suitable for monitoring the freezing process may be used with the cryoliposuction apparatus 10. In one embodiment, a plurality of warm pads 70 are perfused with warm fluid and disposed on surfaces of the monitoring probes 38. The warm pads 70 and the monitoring probes 38 are then placed on the body near the cryosurgical probe 14 to prevent adjacent skin area from freezing during cryoliposuction. The warm pads 70 may be connected to a source of warm fluid 71, and flow of the warm fluid to the pads 70 may be controlled.

Figure 2:
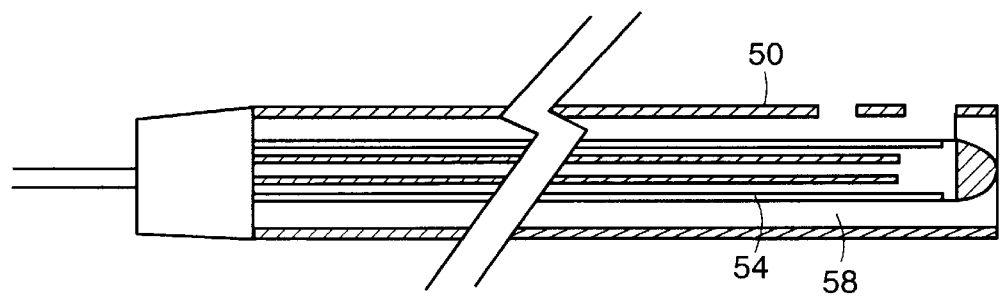
FIG. 2 shows a cross-section of one embodiment of a cryoliposuction probe of the present invention.

Referring to FIG. 2, the first probe and the second probe of the cryoliposuction apparatus may be assembled into a single unit. In this embodiment, an external sleeve 50 fits around a probe 54. The probe 54 may be a cryosurgical probe, and the sleeve 50 and the probe 54 may form a passageway 58 for removing destroyed tissue.

Figure 3:
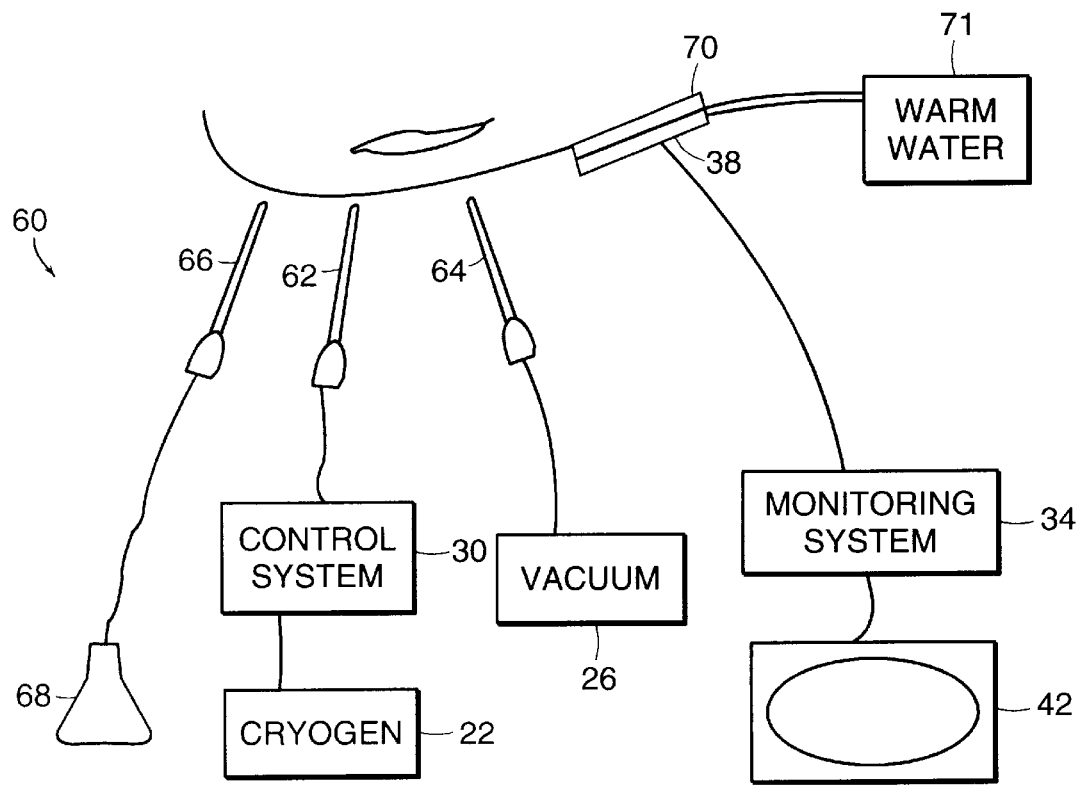
FIG. 3 shows another embodiment of a cryoliposuction apparatus of the present invention.

Referring to FIG. 3, the cryoliposuction apparatus 60 includes a first probe 62, a second probe 64, and a third probe 66. The first probe 62 destroys the tissue by freezing it, and the second probe 64 removes the destroyed tissue. The third probe 66 is in communication with a tumescent fluid 68 and is used for inserting the tumescent fluid into the fatty tissue . The tumescent fluid provides two benefits. One, the fluid acts as a local anesthetic. Two, the fluid comprises a chemical capable of assisting in destroyed the fatty tissue. An example of the tumescent fluid is combination of lidocaine and epinephrine. Alternatively, the second probe 64 may be used for both inserting a tumescent fluid into the fatty tissue and for removing destroyed fatty tissue.

The cryoliposuction apparatus of the present invention may be used in any of the following manner to perform liposuction. Referring to FIG. 1, an incision on the skin 13 is made to provide access to the fatty tissue 11 to be removed. The first probe 14 or the cryosurgical probe of the cryoliposuction apparatus 10 is inserted in the fatty tissue 11. Cryogen from the cryogen source 22 is delivered to the tip of the first probe 14, and the fatty tissue 11 in contact with the probe 14 begins to freeze. The rate of freezing or the freezing interface propagation is in the order of approximately several millimeters per minute. In this manner, freezing of the fatty tissue 11 can be controlled. Once the fatty tissue 11 has been destroyed, the fatty tissue 11 is removed from the body. In one embodiment, a conventional liposuction is performed to remove the destroyed fatty tissue 11. The second probe 18 or the liposuction probe connected to a vacuum source 26 is inserted in the destroyed fatty tissue 11, and aspiration of the destroyed fatty tissue 11 is performed. In another embodiment, the destroyed fatty tissue 11 is left in the body for the body's natural immune system to remove. When a limited amount of fat is destroyed, as for example in a face, cryosurgery of the fat without aspiration may be sulecient to remove the destroyed fat.

In one embodiment, the process of freezing is monitored to control the extent of freezing. The freezing process can be monitored using palpation, image monitoring or temperature monitoring. Examples of suitable image monitoring processes are magnetic resonance imaging, CT imaging and ultrasound imaging. In another embodiment, heat is applied to skin area 13 surrounding the fatty tissue 11 in order to prevent the skin area 13 from freezing. Heat may be applied by placing warm pads 70 perfused with warm fluid on surfaces of the monitoring probes 38 and placing the probes 38 on the body before inserting the cryosurgical probe 14 in the fatty tissue 11. In still another embodiment, a tumescent fluid is introduced into the fatty tissue 11 prior to or after freezing the fatty tissue 11.

Experiments

Experiment 1

This experiment demonstrates that cryosurgery facilitates controlled and easy destruction of fatty tissue. To this end, experiment was performed on the back fat of piglets. An incision was made on the back of a piglet to expose a fatty tissue. A circular region of the fatty tissue having a diameter of about 1 cm was frozen with a 3.5 mm cryosurgical probe, manufactured by Candela Corporation of Wayland, Mass. The tissue froze in the shape of a cylinder. Freezing was controlled by monitoring with an ultrasound surface probe. After freezing and thawing, the tissue was resected in a direction normal to the axis of the frozen cylinder, and the treated area was fixed in formalin for histological examination. The results showed that fat cells and connective tissue in an area that roughly corresponds to the extent of tissue damage as seen under ultrasound imaging were destroyed. Follow up studies performed over a period of six weeks showed that scar tissue formed and replaced the fatty tissue. Thus, this experiment further showed that cryosurgery, in conjunction with the body's own immune system, can be used for destroying and removing fat.

Experiment 2

This experiment demonstrates that cryosurgery facilitates controlled and easier removal of fatty tissue. To this end, experiments were performed on the back fat of pigs.

In the first part of this experiment, a 3 mm aspiration needle connected to a controlled vacuum pump was introduced in the fatty layer of a pig, and a standard liposuction was performed. After the procedure, the treated tissue region was immediately resected, and the treated area was fixed in formalin for histological examination. The results showed that a relatively small amount of fat was removed by simple aspiration and that there was significant bleeding.

In the second part of the experiment, tissue was first frozen as described in Experiment 1. After freezing, the cryosurgical probe was removed, and through the same incision, a 3 mm aspiration needle was introduced into the center of the frozen circular region. The aspiration needle entered the fatty tissue with tremendous ease. In performing liposuction, physicians encounter difficulty in inserting the liposuction probes into the fat. This makes a standard liposuction procedure physically demanding for the physicians. When the fat was first frozen prior to liposuction, however, there was no difficulty in inserting the liposuction probe. After applying the vacuum pump for similar extent of time as in the first part of the experiment, the tissue was resected, fixed in formalin and examined histologically. The results showed that aspiration removes a significantly larger amount of fatty tissue when prior cryosurgery is performed.

Experiment 3

Experiment 3 demonstrates the ability to control the amount of tissue removed with cryoliposuction.

The experimental steps comprise: (1) introducing a 3.5 mm cryosurgical probe in the fatty tissue through an incision; (2) freezing a 1 cm diameter circular region of fat under ultrasound monitoring; (3) removing the cryosurgical probe; (4) introducing an aspiration needle to the tissue through the same incision; and (5) sweeping the aspiration needle connected to a vacuum pump over the previously frozen tissue region under ultrasound monitoring. After the procedure is completed, the tissue is resected, embedded in formalin and examined with histological examination. The results would show that the extent of fatty tissue that has been removed corresponds to the extent of the frozen region observed under ultrasound imaging.

Experiment 4

This experiment demonstrates the feasibility of using cryosurgery as a fat conditioning step prior to liposuction and also as an alternative to liposuction in removing fatty tissue.

Two saws were used in this experiment. Fourteen sub-experiments were performed on different sites of the animal adipose, using cryosurgery, cryoliposuction and liposuction.

In the first part of the experiment, two sites were treated with standard liposuction by: (1) making an incision on the animal skin to provide access to a fatty tissue; (2) inserting a 3.5 mm diameter 20 cm long cylindrical liposuction probe into the fatty tissue under palpation; (3) introducing a tumescent fluid to the fatty tissue through the liposuction probe; and (4) removing the fatty tissue through aspiration.

In the second part of the experiment, six sites were treated with cryosurgery by: (1) making an incision on the animal skin to provide access to a fatty tissue; (2) inserting a cryosurgical probe into the fatty tissue; and (3) freezing the fatty tissue under ultrasound monitoring.

In the third part of the experiment, two sites were treated with cryoliposuction. Cryosurgery was first performed on the sites as described above with respect to the second part of the experiment, and liposuction was subsequently performed to remove the fatty tissue previously destroyed by cryosurgery as described above with respect to the first part of the experiment.

The results showed that microscopic appearances of the tissue treated by liposuction and tissue treated by cryoliposuction were similar. They both induced an inflammatory response, which eventually replaced the damaged fat cells with fibrous connective tissue. Cryoliposuction, however, has the advantage over the standard liposuction in that cryoliposuction allows treatment area to be viewed and treatment process to be controlled under ultrasonic monitoring. In addition, cryosurgery prior to liposuction facilities insertion of the aspiration needle to the fatty tissue such that the aspiration process is not strenuous for the physicians. The results further showed that cryosurgery alone can be used to remove the fatty tissue. Monitoring of the fatty tissue treated by cryosurgery over a six week period showed that most of the fat tissue destroyed by cryosurgery was replaced by dense fibrous connective tissue.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of removing fatty tissue in a body comprising:
   controllably freezing the fatty tissue at a cooling rate sufficient to destroy the fatty tissue; and
   removing the destroyed fatty tissue from the body.

2. The method of claim 1 wherein controllably freezing the fatty tissue comprises:
   inserting a probe in the fatty tissue; and
   internally cooling the probe.

3. The method of claim 1 wherein the probe is a cryosurgical probe, and the probe is internally cooled with a cryogen.

4. The method of claim 1 wherein controllably freezing the fatty tissue comprises freezing at a rate which propagates a freezing interface in the order of approximately several millimeters per minute.

5. The method of claim 1 wherein removing the destroyed fatty tissue comprises performing a conventional liposuction procedure on the destroyed fatty tissue.

6. The method of claim 1 wherein removing the destroyed fatty tissue comprises removal of the destroyed fatty tissue by a body's own immune system.

7. The method of claim 1 wherein removing the destroyed fatty tissue comprises:
   inserting a probe into the destroyed fatty tissue, wherein the probe is connected to a vacuum source; and
   performing an aspiration of the destroyed fatty tissue using the probe and the vacuum.

8. The method of claim 1 further comprising monitoring the freezing process to control the extent of freezing the fatty tissue.

9. The method of claim 8 wherein monitoring comprises monitoring through palpation, image monitoring, or temperature monitoring.

10. The method of claim 9 wherein image monitoring comprises magnetic resonance imaging, CT imaging, light imaging or ultrasound imaging.

11. The method of claim 1 further comprising applying heat to a skin area surrounding the fatty tissue to prevent the skin area from freezing.

12. The method of claim 11 further comprising monitoring the freezing process, wherein monitoring comprises ultrasound imaging using one or more surface monitoring electrodes and applying heat to a skin area comprises placing a warm pad perfused with warm fluid on surfaces of the monitoring electrodes before placing the monitoring electrodes on the body and before mserting the probe into the fatty tissue.

13. The method of claim 11 wherein applying heat to a skin comprises controlling a flow of warm fluid to a skin area underneath the monitoring electrodes.

14. The method of claim 1 further comprising introducing a tumescent fluid in the fatty tissue prior to controllably freezing the fatty tissue.

15. The method of claim 1 further comprising introducing a tumescent fluid in the fatty tissue after controllably freezing the fatty tissue.

16. The method of claim 15 wherein the tumescent fluid comprises a local anesthetic and a chemical capable of destroying fatty tissue.

17. The method of claim 15 wherein the tumescent fluid comprises lidocaine and epinephrine.

18. An improved method of performing liposuction comprising:

applying heat to a skin area outside a fatty tissue to be removed;

controllably freezing the fatty tissue at a cooling rate sufficient to destroy the fatty tissue;

monitoring the freezing process to control the extent of freezing the fatty tissue; and removing the destroyed fatty tissue through a conventional liposuction procedure.

* * * * *